United States Patent
Asagarasu et al.

(10) Patent No.: US 8,101,624 B2
(45) Date of Patent: Jan. 24, 2012

(54) QUINAZOLINE DERIVATIVES

(75) Inventors: Akira Asagarasu, Machida (JP);
  Shuichiro Sato, Komae (JP); Makoto Okada, Inagi (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 57 days.

(21) Appl. No.: 12/310,025

(22) PCT Filed: Jul. 24, 2007

(86) PCT No.: PCT/JP2007/064830
§ 371 (c)(1),
(2), (4) Date: Feb. 6, 2009

(87) PCT Pub. No.: WO2008/018306
PCT Pub. Date: Feb. 14, 2008

(65) Prior Publication Data
US 2009/0318478 A1   Dec. 24, 2009

(30) Foreign Application Priority Data

Aug. 8, 2006  (JP) ................................. 2006-215715

(51) Int. Cl.
*A61K 31/517* (2006.01)
*C07D 401/06* (2006.01)
*C07D 239/88* (2006.01)
(52) U.S. Cl. ........................ 514/266.3; 544/284; 544/287
(58) Field of Classification Search ................ 514/266.3; 544/284, 287
See application file for complete search history.

(56) References Cited

U.S. PATENT DOCUMENTS

| | | | |
|---|---|---|---|
| 4,251,531 A | | 2/1981 | Doria et al. |
| 5,679,677 A | * | 10/1997 | Pill et al. ..................... 514/241 |
| 6,348,474 B1 | * | 2/2002 | Kayakiri et al. .............. 514/303 |
| 6,800,620 B2 | * | 10/2004 | Sadhu et al. .................. 514/183 |
| 6,911,469 B2 | * | 6/2005 | Kayakiri et al. .............. 514/469 |
| 6,943,159 B1 | * | 9/2005 | Gouliaev et al. ............ 514/223.2 |
| 6,967,204 B2 | | 11/2005 | Fryburg et al. |
| 7,060,705 B2 | * | 6/2006 | Fraley et al. ................. 514/266.2 |
| 7,235,548 B2 | * | 6/2007 | Gouliaev et al. ............ 514/223.2 |
| 7,799,775 B2 | * | 9/2010 | Sato et al. .................. 514/222.2 |
| 2003/0195205 A1 | | 10/2003 | DeNinno et al. |
| 2004/0023989 A1 | | 2/2004 | Fryburg et al. |
| 2004/0176361 A1 | | 9/2004 | Fujio et al. |
| 2005/0070557 A1 | | 3/2005 | Fryburg et al. |
| 2006/0106035 A1 | | 5/2006 | Hendrix et al. |

FOREIGN PATENT DOCUMENTS

| | | |
|---|---|---|
| EP | 1 396 488 | 3/2004 |
| JP | 52-71485 | 6/1977 |
| JP | 2005-508978 | 4/2005 |
| JP | 2005-511575 | 4/2005 |
| JP | 2006-507242 | 3/2006 |
| WO | 99/00372 | 1/1999 |
| WO | 02/094790 | 11/2002 |
| WO | 03/037432 | 5/2003 |
| WO | 03/037899 | 5/2003 |
| WO | 2004/018474 | 3/2004 |

OTHER PUBLICATIONS

Kayakiri et al. (Abstract of WO 9900372, CAPLUS, Document No. 130:125067).*
International Search Report issued Sep. 4, 2007 in the International (PCT) Application PCT/JP2007/064830 of which the present application is the U.S. National Stage.
Kovtunenko et al., "2-(4-oxo-3,4-dihydro-2-quinazolinyl-methyl)benzoic acids," Chemistry of Heterocyclic Compounds, 2002, vol. 38, No. 10, pp. 1242-1249.
Fisher et al., "Isolation and Characterization of PDE9A, a Novel Human cGMP-specific Phosphodiesterase," J. Biol. Chem., 1998, vol. 273, No. 25, pp. 15559-15564.
International Preliminary Report on Patentability and Written Opinion issued Feb. 19, 2009 in the International (PCT) Application PCT/JP2007/064830 of which the present application is the U.S. National Stage.
Supplementary European Search Report issued Jul. 6, 2010 in connection with corresponding European Application No. 07 79 1524.

* cited by examiner

*Primary Examiner* — Sabiha Qazi
(74) *Attorney, Agent, or Firm* — Wenderoth, Lind & Ponack, L.L.P.

(57) ABSTRACT

The invention discloses quinazoline derivatives or salts thereof, which possess PDE9-inhibiting activity and are useful as treating agents of dysuria and the like, the derivatives being represented by the formula (I)

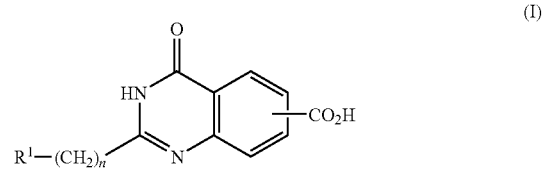

(I)

in the formula, $R^1$ stands for phenyl or aromatic heterocyclic group which are optionally substituted with 1-3 substituents selected from halogen, $C_{1-6}$ alkyl, $C_{1-6}$ haloalkyl containing 1-6 halogen atoms and $C_{1-6}$ alkoxy; and n is an integer of 1-3.

7 Claims, No Drawings

QUINAZOLINE DERIVATIVES

TECHNICAL FIELD

This invention relates to novel quinazoline derivatives and salts thereof, which exhibit phosphodiesterase type 9 (PDE9)-inhibiting activity and are useful as treating agent of dysuria and the like.

BACKGROUND ART

Dysuria can be largely divided into emptying disorder due to inability to urinate with sufficient force at the time of emptying the bladder, and bladder-filling disorder due to inability to retain urine during the filling time. Presently, $\alpha_1$ blocker is frequently used for treating the emptying disorder and anticholine agent, for treating bladder-filling disorder. These drugs, however, have such defects as insufficient long-term therapeutic effect or reduction in quality of life (QOL) induced by side effect, and development of drugs having new activity mechanism different from the conventional approach, for example, drugs utilizing potassium channel opening activity, cyclic guanylate monophosphate (cGMP) decomposition inhibiting activity, are in demand.

cGMP plays an important role in variegated cellular events such as smooth muscle relaxation, memory and learning function control, photoreaction of retina, cell proliferation, immunoreaction and the like, and drop in intracellular cGMP concentration causes disorder in cell functions. Synthesis of cGMP by nitrogen monoxide (NO)-cGMP system and decomposition of cGMP by PDE system are continually progressing in the cells each at a constant rate and good balance of the two are maintained in normal cells. Whereas, within the cells under various states of disorder, function of the NO-cGMP system lowers to render the cGMP synthesis level in the cells low. Because the cGMP decomposition in the cells progresses at a fixed rate in the meantime, cGMP concentration in the affected cells becomes low. It is expected, therefore, prevention of cGMP decomposition in the cells to redress the reduction in intracellular cGMP concentration would be useful for treating or preventing diseases.

While there are many types of PDE, those which specifically decompose cGMP are type 5 (PDE5), type 6 (PDE6) and type 9 (PDE9). Of these, PDE9 shows the least Km value (J. Biol. Chemistry, Vol. 273, No. 25, 15559-15564 (1998), has high affinity to cGMP and is considered to participate in decomposition of cGMP with particular significance.

Heretofore, pyrazolopyrimidine derivatives are known as the compounds exhibiting PDE9-inhibiting activity, and it has been reported as to the derivatives, for example, that they are useful for treating insulin-resistant diseases or the circulatory system disorder, or for improving perception, learning and memory functions (cf. PCT International Publications WO 03/037432 Pamphlet, WO 03/037899 Pamphlet and WO 2004/018474 Pamphlet).

There exists no literature discussing relevancy of PDE9 inhibiting action to therapeutic efficacy of dysuria, however, and not a single quinazoline derivative having PDE9-inhibiting activity is known.

On the other hand, PCT International Publication WO 99/00372 Pamphlet (hereafter referred to as "Literature A") relates to sulfonamide compounds having PDE5-inhibiting activity, in which 7-carboxy-2-(2,4-dichlorobenzyl)-3-methyl-4(3H)-quinazolinone is specifically disclosed as an intermediate product of their synthesis (cf. Literature A, p. 154, Production Example 43-3). Literature A, however, does not disclose a compound in which the 3-position of quinazoline ring is hydrogen atom and does not contain any description or suggestion on PDE9-inhibiting activity of the compound. We also synthesized 7-carboxy-2-(3-chlorobenzyl)-3-methyl-4(3H)-quinazolinone (hereafter referred to as "Compound A") and compared PDE9-inhibiting activity of Compound A with that of a compound in which the 3-position of quinazoline ring is hydrogen atom (i.e., the compound of later appearing Example 1) to find the PDE 9-inhibiting activity of Compound A was less than 1/100 that of the compound of the later appearing Example 1, and was extremely low (cf. later appearing Table A showing PDE 9-inhibiting activity of those compounds).

DISCLOSURE OF THE INVENTION

The object of the present invention is to provide novel quinazoline derivatives which have PDE9-inhibiting activity and are useful as treating agent of disorders including dysuria.

We have discovered, after ardent research activities, that inhibition of PDE9 is effective for treating dysuria such as overactive bladder syndrome, pollakiuria, urinary incontinence, dysuria in benign prostatic hyperplasia and various diseases relating to urinary tract such as urolithiasis. Based on this discovery, we have succeeded in making novel thienopyrimidine derivatives having PDE9-inhibiting activity which are useful as dysuria-treating agent, and come to complete the present invention.

According to the present invention, therefore, quinazoline derivatives represented by the formula (I)

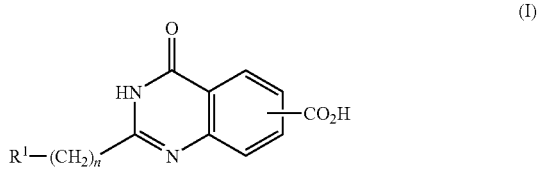

(I)

in the formula,
$R^1$ stands for phenyl or aromatic heterocyclic group which are optionally substituted with 1-3 substituents selected from halogen, $C_{1-6}$ alkyl, $C_{1-6}$ haloalkyl containing 1-6 halogen atoms and $C_{1-6}$ alkoxy; and
n is an integer of 1-3
or salts thereof.

In the present specification, the term "$C_{1-6}$" indicates that the carbon number in the groups to which this term is attached is within the range of given numerals.

"$C_{1-6}$ alkyl" may be straight chain or branched, examples of which include methyl, ethyl, n-propyl, isopropyl, n-butyl, isobutyl, sec-butyl, tert-butyl, n-pentyl and n-hexyl. Of these, methyl, ethyl, n-propyl, isopropyl and n-butyl are preferred.

"$C_{1-6}$ haloalkyl containing 1-6 halogen atoms" signifies $C_{1-6}$ alkyl substituted with same or different 1-6 halogen atoms, examples of which include fluoromethyl, trifluoromethyl, 1,2-dichloroethyl, 1-chloro-2-bromoethyl, pentafluoroethyl, 1-chloro-n-propyl, 2-bromo-2-methylethyl, 3-chloro-n-pentyl, 2-bromo-3-chloro-n-hexyl and the like groups. Of these, $C_{1-2}$ alkyl substituted with same or different 1-5 halogen atoms are preferred.

"$C_{1-6}$ alkoxy" signifies oxy (O) group to which $C_{1-6}$ alkyl is bound, of which specific examples include methoxy, ethoxy, n-propoxy, isopropoxy, n-butoxy, isobutoxy, sec-butoxy, tert-butoxy, n-pentyloxy and n-hexyloxy. Of those, methoxy, ethoxy, n-propoxy, isopropoxy and n-butoxy are preferred.

Furthermore, "halogen" encompasses fluorine, chlorine, bromine and iodine atoms, among which fluorine, chlorine and bromine atoms are preferred.

The "aromatic heterocyclic group" in the definition of $R^1$ in the formula (I) encompasses monocyclic or polycyclic aromatic heterocyclic groups each having 1 or 2 hetero atoms selected from N, O and S and the monocycle or one of the polycycles therein being 5- or 6-membered, specific examples of which include pyrrolyl, furyl, thienyl, imidazolyl, pyrazolyl, oxazolyl, isoxazolyl, thiazolyl, pyridyl, pyrazinyl, pyrimidinyl, pyridazinyl, indolyl, benzimidazolyl, benzoxazolyl, benzthiazolyl, quinolyl, isoquinolyl and quinazolyl. Of these, monocyclic aromatic heterocyclic groups are preferred.

In the formula (I), the substitution site of the carboxyl group on the benzene ring forming the quinazoline skeletal structure is not particularly limited, while the preferred site is 6- or 7-position of quinazoline, in particular, 7-position.

A group of the compounds preferred in the present invention are those represented by the formula (I), in which $R^1$ stands for phenyl which is optionally substituted with 1-3 substituents selected from halogen, $C_{1-6}$ alkyl, $C_{1-6}$ haloalkyl containing 1-6 halogen atoms and $C_{1-6}$ alkoxy.

Another group of the compounds preferred in the invention are those of the formula (I) in which n is 1.

As the typical examples of the compounds of the formula (I) offered by the invention, the following can be named, besides those in the later appearing Examples:

2-benzyl-4-oxo-3,4-dihydroquinazoline-7-carboxylic acid,
2-(2-methylbenzyl)-4-oxo-3,4-dihydroquinazoline-7-carboxylic acid,
2-(3-methylbenzyl)-4-oxo-3,4-dihydroquinazoline-7-carboxylic acid,
2-(3-ethylbenzyl)-4-oxo-3,4-dihydroquinazoline-7-carboxylic acid,
2-(3-isopropylbenzyl)-4-oxo-3,4-dihydroquinazoline-7-carboxylic acid,
2-(4-methylbenzyl)-4-oxo-3,4-dihydroquinazoline-7-carboxylic acid,
2-(4-methoxybenzyl)-4-oxo-3,4-dihydroquinazoline-7-carboxylic acid,
2-(2-ethoxybenzyl)-4-oxo-3,4-dihydroquinazoline-7-carboxylic acid,
2-(3-ethoxybenzyl)-4-oxo-3,4-dihydroquinazoline-7-carboxylic acid,
2-(4-ethoxybenzyl)-4-oxo-3,4-dihydroquinazoline-7-carboxylic acid,
2-(3-tert-butoxybenzyl)-4-oxo-3,4-dihydroquinazoline-7-carboxylic acid,
4-oxo-2-(2-trifluoromethylbenzyl)-3,4-dihydroquinazoline-7-carboxilic acid,
4-oxo-2-(3-trifluoromethylbenzyl)-3,4-dihydroquinazoline-7-carboxylic acid,
4-oxo-2-(4-trifluoromethylbenzyl)-3,4-dihydroquinazoline-7-carboxylic acid,
2-(2-fluorobenzyl)-4-oxo-3,4-dihydroquinazoline-7-carboxylic acid,
2-(3-fluorobenzyl)-4-oxo-3,4-dihydroquinazoline-7-carboxylic acid,
2-(4-fluorobenzyl)-4-oxo-3,4-dihydroquinazoline-7-carboxylic acid,
2-(2-bromobenzyl)-4-oxo-3,4-dihydroquinazoline-7-carboxylic acid,
2-(3-bromobenzyl)-4-oxo-3,4-dihydroquinazoline-7-carboxylic acid,
2-(4-bromobenzyl)-4-oxo-3,4-dihydroquinazoline-7-carboxylic acid,
2-(2-chlorobenzyl)-4-oxo-3,4-dihydroquinazoline-7-carboxylic acid,
2-(4-chlorobenzyl)-4-oxo-3,4-dihydroquinazoline-7-carboxylic acid,
2-(4-fluoro-3-trifluoromethylbenzyl)-4-oxo-3,4-dihydroquinazoline-7-carboxylic acid,
2-(2,3-difluorobenzyl)-4-oxo-3,4-dihydroquinazoline-7-carboxylic acid,
2-(2,4-difluorobenzyl)-4-oxo-3,4-dihydroquinazoline-7-carboxylic acid,
2-(2,5-difluorobenzyl)-4-oxo-3,4-dihydroquinazoline-7-carboxylic acid,
2-(2,6-difluorobenzyl)-4-oxo-3,4-dihydroquinazoline-7-carboxylic acid,
2-(3,4-difluorobenzyl)-4-oxo-3,4-dihydroquinazoline-7-carboxylic acid,
2-(3-chloro-2-fluorobenzyl)-4-oxo-3,4-dihydroquinazoline-7-carboxylic acid,
2-(4-chloro-2-fluorobenzyl)-4-oxo-3,4-dihydroquinazoline-7-carboxylic acid,
2-(5-chloro-2-fluorobenzyl)-4-oxo-3,4-dihydroquinazoline-7-carboxylic acid,
2-(4-chloro-3-fluorobenzyl)-4-oxo-3,4-dihydroquinazoline-7-carboxylic acid,
2-(2-chloro-4-fluorobenzyl)-4-oxo-3,4-dihydroquinazoline-7-carboxylic acid,
2-(3-chloro-4-fluorobenzyl)-4-oxo-3,4-dihydroquinazoline-7-carboxylic acid,
2-(3-bromo-4-fluorobenzyl)-4-oxo-3,4-dihydroquinazoline-7-carboxylic acid,
2-(2,6-dichlorobenzyl)-4-oxo-3,4-dihydroquinazoline-7-carboxylic acid,
2-(2,5-dichlorobenzyl)-4-oxo-3,4-dihydroquinazoline-7-carboxylic acid,
2-(3,5-dichlorobenzyl)-4-oxo-3,4-dihydroquinazoline-7-carboxylic acid,
4-oxo-2-(2,3,4-trifluorobenzyl)-3,4-dihydroquinazoline-7-carboxylic acid,
4-oxo-2-(2,4,5-trifluorobenzyl)-3,4-dihydroquinazoline-7-carboxylic acid,
4-oxo-2-(2,4,6-trifluorobenzyl)-3,4-dihydroquinazoline-7-carboxylic acid,
4-oxo-2-(3,4,5-trifluorobenzyl)-3,4-dihydroquinazoline-7-carboxylic acid,
2-(2-fluoro-4-methoxybenzyl)-4-oxo-3,4-dihydroquinazoline-7-carboxylic acid,
2-(4-fluoro-3-methoxybenzyl)-4-oxo-3,4-dihydroquinazoline-7-carboxylic acid,
2-(2,3-dimethoxybenzyl)-4-oxo-3,4-dihydroquinazoline-7-carboxylic acid,
2-(2,6-dimethoxybenzyl)-4-oxo-3,4-dihydroquinazoline-7-carboxylic acid,
2-(2-fluoro-5-methylbenzyl)-4-oxo-3,4-dihydroquinazoline-7-carboxylic acid,
2-(3-fluoro-4-methylbenzyl)-4-oxo-3,4-dihydroquinazoline-7-carboxylic acid,
2-(4-fluoro-3-methylbenzyl)-4-oxo-3,4-dihydroquinazoline-7-carboxylic acid,
2-(4-chloro-3-methylbenzyl)-4-oxo-3,4-dihydroquinazoline-7-carboxylic acid,
2-(4-methoxy-3-methylbenzyl)-4-oxo-3,4-dihydro-quinazoline-7-carboxylic acid,
2-(2,3-dimethylbenzyl)-4-oxo-3,4-dihydroquinazoline-7-carboxylic acid,
2-(2,5-dimethylbenzyl)-4-oxo-3,4-dihydroquinazoline-7-carboxylic acid, 2-(3,4-dimethylbenzyl)-4-oxo-3,4-dihydroquinazoline-7-carboxylic acid,
2-(3,5-dimethylbenzyl)-4-oxo-3,4-dihydroquinazoline-7-carboxylic acid,
2-(2,6-dimethylbenzyl)-4-oxo-3,4-dihydroquinazoline-7-carboxylic acid,
2-[2-(6-chloropyridylmethyl)]-4-oxo-3,4-dihydroquinazoline-7-carboxylic acid,
2-[2-(5,6-dichloropyridylmethyl)]-4-oxo-3,4-dihydroquinazoline-7-carboxylic acid,
2-[3-(6-chloropyridylmethyl)-4-oxo-3,4-dihydroquinazoline-7-carboxylic acid,
2-[3-(5,6-dichloropyridylmethyl)]-4-oxo-3,4-dihydroquinazoline-7-carboxylic acid,
2-[2-(6-methoxypyridylmethyl)]-4-oxo-3,4-dihydroquinazoline-7-carboxylic acid,
2-[2-(5,6-dimethoxypyridylmethyl)]-4-oxo-3,4-dihydroquinazoline-7-carboxylic acid,
2-[3-(6-methoxypyridylmethyl)]-4-oxo-3,4-dihydroquinazoline-7-carboxylic acid,
2-[3-(5,6-dimethoxypyridylmethyl)]-4-oxo-3,4-dihydroquinazoline-7-carboxylic acid,
4-oxo-2-(3-thienylmethyl)-3,4-dihydroquinazoline-7-carboxilic acid,
2-[2-(5-chlorothienylmethyl)]-4-oxo-3,4-dihydroquinazoline-7-carboxylic acid,
2-[2-(5-methoxythienylmethyl)]-4-oxo-3,4-dihydroquinazoline-7-carboxylic acid,
2-benzyl-4-oxo-3,4-dihydroquinazoline-6-carboxylic acid,
2-(3,4-dichlorobenzyl)-4-oxo-3,4-dihydroquinazoline-6-carboxylic acid,
2-(3,4-dimethoxybenzyl)-4-oxo-3,4-dihydroquinazoline-6-carboxylic acid,
2-(2-methoxybenzyl)-4-oxo-3,4-dihydroquinazoline-6-carboxylic acid,
2-(3-methoxybenzyl)-4-oxo-3,4-dihydroquinazoline-6-carboxylic acid,
2-(3-chlorobenzyl)-4-oxo-3,4-dihydroquinazoline-6-carboxylic acid,
4-oxo-2-(2-pyridylmethyl)-3,4-dihydroquinazoline-6-carboxylic acid,
4-oxo-2-(3-pyridylmethyl)-3,4-dihydroquinazoline-6-carboxylic acid,
4-oxo-2-(2-thienylmethyl)-3,4-dihydroquinazoline-6-carboxylic acid,
2-benzyl-4-oxo-3,4-dihydroquinazoline-5-carboxylic acid,
2-(3,4-dichlorobenzyl)-4-oxo-3,4-dihydroquinazoline-5-carboxylic acid,
2-(3,4-dimethoxybenzyl)-4-oxo-3,4-dihydroquinazoline-5-carboxylic acid,
2-(2-methoxybenzyl)-4-oxo-3,4-dihydroquinazoline-5-carboxylic acid,
2-(3-methoxybenzyl)-4-oxo-3,4-dihydroquinazoline-5-carboxylic acid,
2-(3-chlorobenzyl)-4-oxo-3,4-dihydroquinazoline-5-carboxylic acid,
4-oxo-2-(2-pyridylmethyl)-3,4-dihydroquinazoline-5-carboxylic acid,
4-oxo-2-(3-pyridylmethyl)-3,4-dihydroquinazoline-5-carboxylic acid,
4-oxo-2-(2-thienylmethyl)-3,4-dihydroquinazoline-5-carboxylic acid,
2-benzyl-4-oxo-3,4-dihydroquinazoline-8-carboxylic acid,
2-(3,4-dichlorobenzyl)-4-oxo-3,4-dihydroquinazoline-8-carboxylic acid,
2-(3,4-dimethoxybenzyl)-4-oxo-3,4-dihydroquinazoline-8-carboxylic acid,
2-(2-methoxybenzyl)-4-oxo-3,4-dihydroquinazoline-8-carboxylic acid,
2-(3-methoxybenzyl)-4-oxo-3,4-dihydroquinazoline-8-carboxylic acid,
2-(3-chlorobenzyl)-4-oxo-3,4-dihydroquinazoline-8-carboxylic acid,
4-oxo-2-(2-pyridylmethyl)-3,4-dihydroquinazoline-8-carboxylic acid,
4-oxo-2-(3-pyridylmethyl)-3,4-dihydroquinazoline-8-carboxylic acid,
4-oxo-2-(2-thienylmethyl)-3,4-dihydroquinazoline-8-carboxylic acid,
4-oxo-2-phenethyl-3,4-dihydroquinazoline-7-carboxilic acid,
2-(3,4-dichlorophenethyl)-4-oxo-3,4-dihydroquinazoline-7-carboxylic acid,
2-(3,4-dimethoxyphenethyl)-4-oxo-3,4-dihydroquinazoline-7-carboxylic acid,
2-(2-methoxyphenethyl)-4-oxo-3,4-dihydroquinazoline-7-carboxylic acid,
2-(3-methoxyphenethyl)-4-oxo-3,4-dihydroquinazoline-7-carboxylic acid,
2-(3-chlorophenethyl)-4-oxo-3,4-dihydroquinazoline-7-carboxylic acid,
4-oxo-2-[2-(2-pyridyl)ethyl]-3,4-dihydroquinazoline-7-carboxylic acid,
4-oxo-2-[2-(3-pyridyl)ethyl]-3,4-dihydroquinazoline-7-carboxylic acid,
4-oxo-2-[2-(2-thienyl)ethyl]-3,4-dihydroquinazoline-7-carboxylic acid,
4-oxo-2-(3-phenylpropyl)-3,4-dihydroquinazoline-7-carboxylic acid,
2-[3-(3,4-dimethoxyphenyl)propyl]-4-oxo-3,4-dihydroquinazoline-7-carboxylic acid,
2-[3-(2-methoxyphenyl)propyl]-4-oxo-3,4-dihydroquinazoline-7-carboxylic acid,
2-[3-(3-methoxyphenyl)propyl]-4-oxo-3,4-dihydroquinazoline-7-carboxylic acid,
2-[3-(3-chlorophenyl)propyl]-4-oxo-3,4-dihydroquinazoline-7-carboxylic acid,
4-oxo-2-[3-(2-pyridyl)propyl]-3,4-dihydroquinazoline-7-carboxylic acid,
4-oxo-2-[3-(3-pyridyl)propyl]-3,4-dihydroquinazoline-7-carboxylic acid, and
4-oxo-2-[3-(2-thienyl)propyl]-3,4-dihydroquinazoline-7-carboxylic acid.

Those compounds of the formula (I) in the present invention can also be in the form of salts, for example, alkali metal salts such as sodium salt, potassium salt, lithium salt and the like; alkaline earth metal salts such as calcium salt, magnesium salt and the like; salts with organic bases such as triethylamine, dicyclohexylamine, pyrrolidine, morpholine, pyridine and the like; and ammonium salts. Of these salts, pharmaceutically acceptable salts are particularly preferred.

According to the present invention, the compounds of the formula (I) can be prepared, for example, by the following method (a). For the particulars such as the reaction conditions, later-appearing Production Example 1 and Example 1 are to be referred to. Method (a): The compounds of the formula (I), i.e., quinazoline derivatives represented by the following formula,

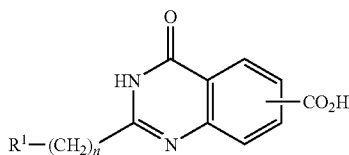

(I)

in the formula, $R^1$ and n have the previously defined significations, can be produced, for example, by reacting anthranilic acid derivatives of the formula,

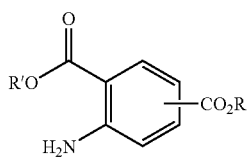

(II)

in the formula, R and R' stand for $C_{1-6}$ alkyl independently of each other, with nitrile compounds of the formula,

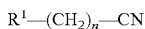

(III)

in the formula, $R^1$ and n have the previously defined significations, and hydrolyzing the ester on the quinazoline ring in the resultant compounds represented by the following formula,

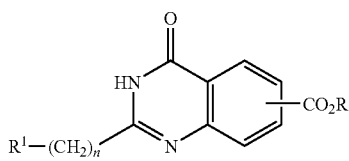

(IV)

in the formula, $R^1$, n and R have the previously defined significations.

The reaction of the anthranilic acid derivatives of the formula (II) with the nitrile compounds of the formula (III) in the above method (a) can be performed generally in inert solvent such as amides including N,N-dimethylformamide and N,N-dimethylacetamide; alcohols including methanol, ethanol and isopropanol; or ethers including tetrahydrofuran and dioxane, in the presence of an acid catalyst such as hydrochloric acid, hydrobromic acid and p-toluenesulfonic acid, at −20° C. to the refluxing temperature of the reaction mixture, preferably at a temperature within a range of 0-80° C.

The use ratio of the nitrile compound of the formula (III) to the compound of the formula (II) is not particularly limited, while it is preferable to use generally at least 1 mol, in particular, within a range of 1.05-5 mols, inter alia, 1.2-2 mols, of the nitrile compound of the formula (III), per mol of the compound of the formula (II). The acid catalyst can be used within a range of about 0.2-about 50 mols, per mol of the compound of the formula (II).

The hydrolysis of the ester on the quinazoline ring in the resulting compound of the formula (IV) can be carried out by per se known method, for example, by suspending or dissolving the compound of the formula (IV) in a mixed solvent of alcohol such as methanol, ethanol or the like with water, at temperatures within a range of 0° C.— refluxing temperature of the reaction mixture, preferably from room temperature to refluxing temperature of the reaction mixture, in the presence of an alkali such as sodium hydroxide, potassium hydroxide, potassium carbonate or the like. The use ratio of the alkali to the compound of the formula (IV) is not critical, but the alkali can be generally used within a range of about 1-20 mols per mol of the compound of the formula (IV).

Those anthranilic acid derivatives of the formula (II) which are used as the starting materials in the reaction of above method (a) are mostly known already and are readily commercially available. Even when a novel anthranilic acid derivative is to be used, it can be easily synthesized from known compounds.

Most of the nitrile compounds of the formula (III) used as the starting materials in the reaction of above method (a) also are known. Even when a novel compound is to be used, it can be easily synthesized following per se known means of synthesis, for example, the method as described in such referential literature: Synthesis, 1980, 150-151 or Bioorg. Med. Chem. Lett., 2002 (12), 1275-1278.

The compounds of the formula (I) produced by the method (a) can be isolated from the reaction mixtures and purified by the means known per se, for example, recrystallization, column chromatography, thin layer chromatography and the like.

Those quinazoline derivatives represented by the formula (I) or salts thereof provided by the present invention exhibit potent PDE9-inhibiting activity, and are useful for therapeutic and treating agents of diseases associated with decomposition of cGMP by PDE9 (PDE-associated diseases), for example, overactive bladder syndrome, pollakiuria, urinary incontinence, dysuria in benign prostatic hyperplasia, neurogenic bladder, interstitial cystitis, urolithiasis, benign prostatic hyperplasia, erectile dysfunction, cognitive impairment, neuropathy, Alzheimer's disease, pulmonary hypertension, chronic obstructive pulmonary disease, ischemic heart disease, hypertension, angina, myocardial infarction, arteriosclerosis, thrombosis, embolism, type 1 diabetes and type 2 diabetes.

Among the quinazoline derivatives represented by the formula (I) and salts thereof that are provided by the present invention, those which exhibit slight PDE5-inhibiting activity in addition to their PDE9-inhibiting activity are expected to achieve also the functional effects based on the PDE5-inhibiting activity.

PDE9-inhibiting activity and PDE5-inhibiting activity of the compounds of the formula (I) and their salts are demonstrated by the following experiments.

(1) Measurement of PDE9-Inhibiting Activity:
1) Preparation of Human Recombinant PDE9 Protein Based on the base sequence of hsPDE9A1 registered with GenBank database (accession No.: AF048837), hsPDE9A1 fragment was amplified by polymerase chain reaction under the following conditions, using the following sequence (Amasham Pharmacia Biotech) as the primer and Human Prostate MATCHMAKER cDNA library (CLONTECH) as the template DNA, with Pfu Turbo DNA polymerase (STRATAGENE):

```
hPDE9-5A primer:
CCTAGCTAGCCACCATGGGATCCGGCTCCTCC hPDE9-3A primer:
TTTTCCTTTTGCGGCCGCTTATTAGGCACAGTCTCCTTCACTG
```

PCR condition: [95° C., 5 min]×1 cycle, [(95° C., 1 min), (58° C., 2 min), (72° C., 3 min)]×25 cycles, [72° C., 10 min]×1 cycle Thus obtained hsPDE9A1 fragment was given a restricted enzymatic treatment with NheI and NotI, and thereafter inserted into pcDNA 3.1(+) expression vector (Invitrogen) to let it serve as a human PDE9 expression vector.

Human PDE9 expression vector-transformed *Escherichia coli* was mass incubated to produce a large amount of human PDE9 expression vector, which was transiently transfected into COS-1 cells, with LIPOFECTAMINE 2000 Reagent (GIBCO). The cells were homogenized in ice-cooled buffer A (40 mmol/L Tris-HCl, pH7.5, 15 mmol/L benzamidine, 15 mmol/L 2-mercaptoethanol, 1 µg/mL Pepstatin A, 1 µg/mL Leupeptin, 5 mmol/L EDTA) and centrifuged at 4° C., 14,000×g for 10 minutes. The supernatant was isolated to provide human recombinant PDE9 protein solution.

2) Measurement of PDE9-Inhibiting Activity

To 150 µL of buffer B (70 mmol/L Tris-HCl, pH7.5; 16.7 mmol/L $MgCl_2$, 33.3 nmol/L [$^3$H]-cGMP) solution containing [$^3$H]-cGMP (specific activity=244.2 GBq/mmol) at a concentration of 33.3 nmol/L, 50 µL of a solution of the compound to be evaluated (formed by dissolving the compound in DMSO and diluting it with distilled water to DMSO concentration of 5%) and 50 µL of the PDE9 protein solution as prepared in the above, as diluted with buffer C (40 mmol/L Tris-HCl, pH7.5, 15 mmol/L benzamidine, 15 mmol/L 2-mercaptoethanol, 1 µg/mL Pepstatin A, 1 µg/mL Leupeptin) by 1,500×, were added under cooling with ice. This mixed solution was incubated at 30° C. for 30 minutes and the enzymatic reaction of PDE9 was terminated by heating the system in boiling water for 90 seconds. Returning the system to room temperature, 50 µL of Snake venom (SIGMA: 1 mg/mL) was added, followed by 10 minutes' incubation at 30° C., to convert the [$^3$H]-5'-GMP produced in the previous reaction to [$^3$H]-guanosine. This reaction solution was passed through a column filled with 1 mL of 0.5 mol/L hydrochloric acid-activated cation-exchange resin (Bio-Rad AG50W-X4 resin, mesh size 200-400) and removed of the unreacted substrate ([$^3$H]-cGMP) by elution with 12 mL of distilled water. Thereafter [$^3$H]-guanosine was eluted with 3 mL of 3 mol/L aqueous ammonia and its radiation activity was measured with liquid scintillation counter.

PDE9 inhibition of the tested compound can be calculated by the following formula:

$$\left[\left(1 - \frac{\text{radiation activity where a test compound is used}}{\text{radiation activity in control test}}\right) \times 100\right]$$

From the percent inhibition at various concentration levels of each tested compound, its $IC_{50}$ value against PDE9 can be determined. The results are shown in Table A given later.

(2) Measurement of PDE5-inhibiting activity:
1) Preparation of Human Recombinant PDE5 Protein Based on the base sequence of hsPDE5A1 registered with GenBank database (accession No.: NM-001083), hsPDE5A1 fragment was amplified by polymerase chain reaction (PCR) under the following conditions, using the following sequence (SIGMA GENOSYS) as the primer and Human Prostate MATCHMAKER cDNA library (CLONTECH) as the template DNA, with KDD plus DNA polymerase (TOYOBO):

hPDE5-5' E primer:    CGGAATTCCAACCATGGAGCGGGC hPDE5-3' primer:     GCTCTAGATCAGTTCCGCTTGGCCTGG PCR condition: [94° C., 2 min]×1 cycle, [(94° C., 30 sec), (65° C., 30 sec), (68° C., 3 min)]×25 cycles, [68° C., 6 min]×1 cycle Thus obtained hsPDE5A1 fragment was given a restricted enzymatic treatment with XBaI and EcoRI, and thereafter inserted into pcDNA 3.1(+) expression vector (Invitrogen) to let it serve as a human PDE5 expression vector.

Human PDE5 expression vector-transformed *Escherichia coli* was mass incubated to produce a large amount of human PDE5 expression vector, which was transiently transfected into COS-1 cells, with LIPOFECTAMINE 2000 Reagent (GIBCO). The cells were homogenized in ice-cooled buffer A and centrifuged at 4° C., 14,000×g for 10 minutes. The supernatant was isolated to provide human recombinant PDE5 protein solution.

2) Measurement of PDE5-Inhibiting Activity

By a method similar to the measurement of PDE9-inhibiting activity, PDE5-inhibiting activity of each of the test compounds was measured, percent inhibition was calculated and $IC_{50}$ value against PDE5 was determined. The results are shown in the following Table A, concurrently with the compounds' $IC_{50}$ values against PDE9.

TABLE A

| Compound | Structural Formula | Inhibiting Activity ($IC_{50}$ value or percent inhibition at 1 µM) | |
| --- | --- | --- | --- |
| | | PDE9 | PDE5 |
| Example 1 | | $IC_{50}$ = 18 nM | $IC_{50}$ = 6,210 nM |
| Example 2 | | $IC_{50}$ = 35 nM | $IC_{50}$ = 1,435 nM |

TABLE A-continued

| Compound | Structural Formula | Inhibiting Activity (IC$_{50}$ value or percent inhibition at 1 μM) | |
|---|---|---|---|
| | | PDE9 | PDE5 |
| Example 3 | [2-(3,4-dimethoxybenzyl)-4-oxo-3H-quinazoline-7-carboxylic acid] | inhibition = 11% | — |
| Example 4 | [2-(2-methoxybenzyl)-4-oxo-3H-quinazoline-7-carboxylic acid] | IC$_{50}$ = 1,290 nM | — |
| Example 5 | [2-(3-methoxybenzyl)-4-oxo-3H-quinazoline-7-carboxylic acid] | inhibition = 41% | — |
| Example 6 | [2-(pyridin-2-ylmethyl)-4-oxo-3H-quinazoline-7-carboxylic acid] | IC$_{50}$ = 1,360 nM | — |
| Example 7 | [2-(pyridin-3-ylmethyl)-4-oxo-3H-quinazoline-7-carboxylic acid] | inhibition = 30% | — |
| Example 8 | [2-(thiophen-2-ylmethyl)-4-oxo-3H-quinazoline-7-carboxylic acid] | IC$_{50}$ = 93 nM | — |
| Referential Example 1 | [2-(3-chlorobenzyl)-3-methyl-4-oxo-3H-quinazoline-7-carboxylic acid] | IC$_{50}$ = 4,659 nM | — |

Thus the quinazoline derivatives represented by the formula (I) of this invention or salts thereof can be administered as PDE9 inhibitor or PDE9 inhibitor concurrently exhibiting slight PDE5-inhibiting activity, for therapy or treatment of PDE9-associated diseases of human and other mammals, orally or parenterally (e.g., intramuscular injection, intravenous injection, rectal administration, percutaneous administration and the like). When PDE5 is inhibited thereby, urethra relaxation is induced, and hence the compounds of the present invention is expected to have an action to reduce residual urine volume, when they have the slight PDE5-inhibiting activity concurrently.

The drugs of the present invention can be formulated, together with non-toxic excipients, any of the preparation forms such as solid (e.g., tablet, hard capsule, soft capsule, granule, powder, fine granule, pill, troche and the like); semi-solid (e.g., suppository, ointment and the like); or liquid (e.g., injection, emulsion, suspension, lotion, spray and the like). As non-toxic excipients useful for such formulations, for example, starch, gelatin, glucose, lactose, fructose, maltose, magnesium carbonate, talc, magnesium stearate, methyl cellulose, carboxymethyl cellulose or salts thereof, gum Arabic, polyethylene glycol, p-hydroxybenzoic acid alkyl ester, syrup, ethanol, propylene glycol, vaseline, Carbowax, glycerine, sodium chloride, sodium sulfite, sodium phosphate, citric acid and the like can be named. These drugs may also contain other therapeutically useful drugs.

Content of the compounds of the formula (I) in these drugs differs depending on such factors as the preparation form and administration route, while generally it can be contained at a concentration of 0.1-50 wt % in solid and semi-solid forms, and of 0.05-10 wt %, in liquid form.

Doses of the compounds of the formula (I) are variable over broad ranges according to the kind of warm-blooded animals including human to be treated, kind of involved disease, administration route, seriousness of symptoms, doctor's diagnosis and so on. Whereas, generally they can be each within a range of 0.01-5 mg/kg, preferably 0.02-2 mg/kg, per day, it being obviously possible to administer doses less than the above lower limit or more than the above upper limit, according to the seriousness of individual patients' symptoms, doctor's diagnosis and so on, as aforesaid. Each dose can be administered single time per day or dividedly plural times per day.

EXAMPLES

Hereinafter the present invention is more specifically explained, referring to Production Examples, working Examples and Formulation Example.

Production Example 1

Methyl 2-(3-chlorobenzyl)-4-oxo-3,4-dihydro-quinazoline-7-carboxylate

A mixture of 628 mg of dimethyl aminoterephthalate, 546 mg of 3-chlorophenylacetonitrile and 15 mL of 4N hydrogen chloride dioxane solution was stirred at room temperature for 7 hours. Further continuing the stirring at 30° C. for 63 hours and at 70° C. for 25 hours, ice was added to the reaction mixture, followed by addition of 7 mL of 25% aqueous ammonia. Whereupon precipitated crystals were recovered by filtration, and washed with water, ether and chloroform by the order stated. Subjecting the crystals to through-flow drying under heating, 670 mg of the title compound was obtained.

$^1$H-NMR (DMSO-$d_6$, δ): 3.91 (3H, s), 3.99 (2H, s), 7.3-7.4 (3H, m), 7.4-7.5 (1H, m), 7.96 (1H, dd, J=1.4, 8.3 Hz), 8.08 (1H, d, J=1.4 Hz), 8.19 (1H, d, J=8.3 Hz), 12.61 (1H, br s).

MS (m/z): 327 (M$^+$−1).

Production Example 2

Methyl 2-(3,4-dichlorobenzyl)-4-oxo-3,4-dihydro-quinazoline-7-carboxylate

420 Milligrams of dimethyl aminoterephthalate and 446 mg of 3,4-dichlorophenylacetonitrile were added to 10 mL of 4N hydrogen chloride dioxane solution and stirred for about 2 days. Pouring the reaction mixture into ice, its pH was adjusted to 8-9 with 25% aqueous ammonia. The precipitated crystals were recovered by filtration and washed with water. The crude crystals were dissolved in chloroform-ethyl acetate (1:1) mixed solvent, and after removing the insoluble matter by filtration, the remaining solution was concentrated. The residue was purified on silica gel column chromatography (hexane:ethyl acetate=4:1) to provide 253 mg of the title compound.

$^1$H-NMR (DMSO-$d_6$, δ): 3.91 (3H, s), 4.00 (2H, s), 7.3-7.4 (1H, m), 7.59 (1H, d, J=8.4 Hz), 7.68 (1H, d, J=2.2 Hz), 7.96 (1H, d, J=8.4 Hz), 8.06 (1H, s), 8.19 (1H, d, J=8.4 Hz).

MS (m/z): 363 (M$^+$+2), 361 (M$^+$, base).

Production Example 3

Methyl 2-(3,4-dimethoxybenzyl)-4-oxo-3,4-dihydro-quinazoline-7-carboxylate

The title compound was obtained in the manner similar to Production Example 2.

$^1$H-NMR (DMSO-$d_6$, δ): 3.71 (3H, s), 3.75 (3H, s), 3.87 (2H, s), 3.91 (3H, s), 6.8-6.9 (2H, m), 7.04 (1H, s), 7.94 (1H, d, J=8.1 Hz), 8.10 (1H, s), 8.18 (1H, d, J=8.4 Hz).

MS (m/z): 354 (M$^+$, base).

Production Example 4

Methyl 2-(2-methoxybenzyl)-4-oxo-3,4-dihydro-quinazoline-7-carboxylate

The title compound was obtained in the manner similar to Production Example 2.

$^1$H-NMR (CDCl$_3$, δ): 3.98 (3H, s), 3.99 (3H, s), 4.08 (2H, s), 6.9-7.1 (2H, m), 7.3-7.4 (2H, m), 8.0-8.1 (1H, m), 8.26 (1H, d, J=8.4 Hz), 8.38 (1H, d, J=1.5 Hz), 9.53 (1H, br s).

MS (m/z): 324 (M$^+$), 293 (base).

Production Example 5

Methyl 2-(3-methoxybenzyl)-4-oxo-3,4-dihydro-quinazoline-7-carboxylate

The title compound was obtained in the manner similar to Production Example 2.

$^1$H-NMR (DMSO-$d_6$, δ): 3.72 (3H, s), 3.90 (3H, s), 3.91 (2H, s), 6.7-6.9 (1H, m), 6.94 (1H, d, J=7.8 Hz), 6.97 (1H, d, J=2.0 Hz), 7.22 (1H, t, J=7.1 Hz), 7.9-8.0 (1H, m), 8.09 (1H, d, J=1.5 Hz), 8.17 (1H, d, J=8.3 Hz), 12.56 (1H, br s).

MS (m/z): 324 (M$^+$), 323 (base).

Production Example 6

Methyl 4-oxo-2-(2-pyridylmethyl)-3,4-dihydro-quinazoline-7-carboxylate

The title compound was obtained in the manner similar to Production Example 2.

$^1$H-NMR (DMSO-$d_6$, δ): 3.89 (3H, s), 4.17 (2H, s), 7.2-7.3 (1H, m), 7.43 (1H, d, J=7.8 Hz), 7.7-7.8 (1H, m), 7.94 (1H, dd, J=2.0, 8.3 Hz), 8.04 (1H, d, J=1.5 Hz), 8.20 (1H, d, J=8.3 Hz), 8.47 (1H, dd, J=1.0, 4.9 Hz), 12.57 (1H, br s).

MS (m/z): 295 (M$^+$), 294 (base).

Production Example 7

Methyl 4-oxo-2-(3-pyridylmethyl)-3,4-dihydro-quinazoline-7-carboxylate

The title compound was obtained in the manner similar to Production Example 2.

$^1$H-NMR (DMSO-$d_6$, δ): 3.94 (3H, s), 4.01 (2H, s), 7.35 (1H, dd, J=4.9, 7.8 Hz), 7.7-7.8 (1H, m), 7.94 (1H, dd, J=1.5, 8.3 Hz), 8.05 (1H, d, J=1.5 Hz), 8.18 (1H, d, J=8.3 Hz), 8.4-8.5 (1H, m), 8.60 (1H, d, J=2.4 Hz), 12.64 (1H, br s).

MS (m/z): 295 (M$^+$), 294 (base).

Production Example 8

Methyl 4-oxo-2-(2-thienylmethyl)-3,4-dihydro-quinazoline-7-carboxylate

The title compound was obtained in the manner similar to Production Example 2.

$^1$H-NMR (DMSO-d$_6$, δ): 3.90 (3H, s), 4.16 (2H, s), 6.97 (1H, dd, J=3.4, 4.9 Hz), 7.0-7.1 (1H, m), 7.39 (1H, dd, J=1.0, 5.4 Hz), 7.9-8.0 (1H, m), 8.10 (1H, d, J=1.5 Hz), 8.19 (1H, d, J=8.3 Hz), 12.61 (1H, br s).

MS (m/z): 300 (M$^+$, base).

Production Example 9

Methyl 2-(3-chlorobenzyl)-3-methyl-4-oxo-3,4-dihydro-quinazoline-7-carboxylate A mixture of 160 mg of methyl 2-(3-chlorobenzyl)-4-oxo-3,4-dihydroquinazoline-7-carboxylate which was synthesized in Production Example 1, 65 mg of potassium carbonate, 20 mL of acetonitrile and 67 mg of methyl iodide was heated for 2 hours under reflux. Further 20 mg of methyl iodide was added, followed by another hour's heating under reflux. The reaction mixture was allowed to cool off, and then concentrated under reduced pressure, 10 mL of water was added thereto, and extracted with 60 mL of ethyl acetate. The organic layer was washed with 10 mL of saturated saline solution, dried over magnesium sulfate, concentrated under reduced pressure, and the residue was purified on silica gel chromatography (hexane:ethyl acetate=2:1) to provide 130 mg of the title compound.

$^1$H-NMR (CDCl$_3$, δ): 3.52 (3H, s), 3.98 (3H, s), 4.23 (2H, s), 7.1-7.4 (4H, m), 8.08 (1H, dd, J=1.5, 8.2 Hz), 8.32 (1H, d, J=8.2 Hz), 8.38 (1H, d, J=1.5 Hz).

MS (m/z): 341 (M$^+$−1, base).

Example 1

2-(3-Chlorobenzyl)-4-oxo-3,4-dihydroquinazoline-7-carboxylic acid

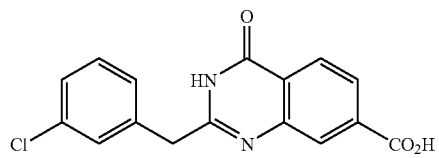

A mixture of 336 mg of methyl 2-(3-chlorobenzyl)-4-oxo-3,4-dihydroquinazoline-7-carboxylate which was synthesized in Production Example 1, 3.0 mL of aqueous 1N sodium hydroxide solution and 6 mL of ethanol was heated for 2.5 hours under reflux. The reaction solution was allowed to cool off, and to which 3.0 mL of 1N hydrochloric acid and 5 mL of water were added. Whereupon precipitated crystals were recovered by filtration, washed with water and through-flow dried under heating, to provide 300 mg of the title compound.

$^1$H-NMR (DMSO-d$_6$, δ): 3.99 (2H, s), 7.3-7.4 (3H, m), 7.4-7.5 (1H, m), 7.95 (1H, dd, J=1.4, 8.3 Hz), 8.07 (1H, d, J=1.4 Hz), 8.17 (1H, d, J=8.3 Hz), 12.58 (1H, br s), 13.40 (1H, br s).

MS (m/z): 313 (M$^+$−1).

Example 2

2-(3,4-Dichlorobenzyl)-4-oxo-3,4-dihydroquinazoline-7-carboxylic acid

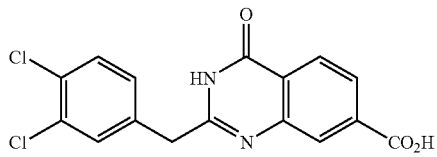

A mixture of 100 mg of methyl 2-(3,4-dichlorobenzyl)-4-oxo-3,4-dihydroquinazoline-7-carboxylate which was synthesized in Production Example 2, 0.5 mL of 1N sodium hydroxide and 1 mL of water was heated under reflux for about 3 hours. After cooling off, 1N hydrochloric acid was added to the reaction solution to render the latter acidic, and the resulting precipitate was recovered by filtration and dried to provide 99 mg of the title compound.

$^1$H-NMR (DMSO-d$_6$, δ): 3.99 (2H, s), 7.38 (1H, dd, J=2.4, 8.3 Hz), 7.59 (1H, d, J=8.3 Hz), 7.68 (1H, d, J=2.0 Hz), 7.9-8.0 (1H, m), 8.05 (1H, d, J=1.5 Hz), 8.17 (1H, d, J=8.3 Hz), 12.56 (1H, br s), 13.41 (1H, br s).

MS (m/z): 349 (M$^+$+2), 347 (M$^+$, base).

Example 3

2-(3,4-Dimethoxybenzyl)-4-oxo-3,4-dihydro-quinazoline-7-carboxylic acid

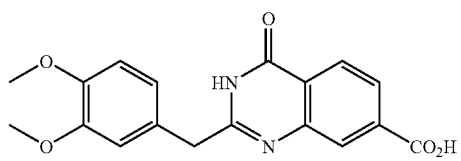

Using methyl 2-(3,4-dimethoxybenzyl)-4-oxo-3,4-dihydro-quinazoline-7-carboxylate which was synthesized in Production Example 3, the title compound was obtained in the manner similar to Example 2.

$^1$H-NMR (DMSO-d$_6$, δ): 3.70 (3H, s), 3.74 (3H, s), 3.86 (2H, s), 6.8-7.0 (2H, m), 7.04 (1H, s), 7.9-8.0 (1H, m), 8.06 (1H, d, J=1.1 Hz), 8.09 (1H, d, J=8.3 Hz), 12.43 (1H, br s).

MS (m/z): 340 (M$^+$, base).

Example 4

2-(2-Methoxybenzyl)-4-oxo-3,4-dihydroquinazoline-7-carboxylic acid

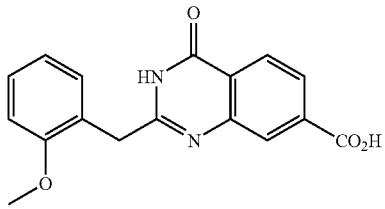

Using methyl 2-(2-methoxybenzyl)-4-oxo-3,4-dihydroquinazoline-7-carboxylate which was synthesized in Production Example 4, the title compound was synthesized in the manner similar to Example 2.

$^1$H-NMR (DMSO-$d_6$, δ): 3.75 (3H, s), 3.93 (2H, s), 6.89 (1H, dt, J=0.8, 7.4 Hz), 6.98 (1H, d, J=8.1 Hz), 7.1-7.2 (1H, m), 7.2-7.3 (1H, m), 7.91 (1H, dd, J=1.6, 8.1 Hz), 7.97 (1H, d, J=1.2 Hz), 8.17 (1H, d, J=8.1 Hz), 12.42 (1H, br s), 13.34 (1H, br s).

MS (m/z): 310 (M$^+$), 279 (base).

Example 5

2-(3-Methoxybenzyl)-4-oxo-3,4-dihydroquinazoline-7-carboxylic acid

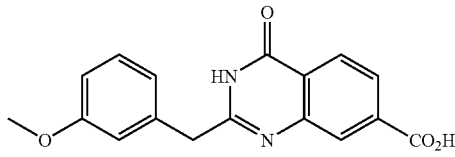

Using methyl 2-(3-methoxybenzyl)-4-oxo-3,4-dihydroquinazoline-7-carboxylate which was synthesized in Production Example 5, the title compound was obtained in the manner similar to Example 2.

$^1$H-NMR (DMSO-$d_6$, δ): 3.72 (3H, s), 3.90 (2H, s), 6.8-6.9 (1H, m), 6.94 (1H, d, J=7.7 Hz), 6.9-7.0 (1H, m), 7.22 (1H, t, J=7.9 Hz), 7.92 (1H, dd, J=1.5, 8.3 Hz), 8.07 (1H, d, J=1.5 Hz), 8.15 (1H, d, J=8.3 Hz), 12.53 (1H, br s), 13.37 (1H, br s).

MS (m/z): 310 (M$^+$), 309 (base).

Example 6

4-Oxo-2-(2-pyridylmethyl)-3,4-dihydroquinazoline-7-carboxylic acid

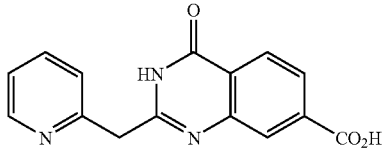

Using methyl 4-oxo-2-(2-pyridylmethyl)-3,4-dihydroquinazoline-7-carboxylate which was synthesized in Production Example 6, the title compound was in the manner similar to Example 2.

MS (m/z): 281 (M$^+$), 280 (base).

Example 7

4-Oxo-2-(3-pyridylmethyl)-3,4-dihydroquinazoline-7-carboxylic acid

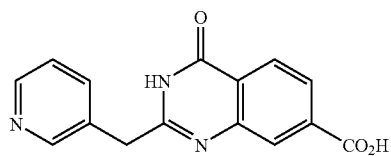

Using methyl 4-oxo-2-(3-pyridylmethyl)-3,4-dihydroquinazoline-7-carboxylate which was synthesized in Production Example 7, the title compound was synthesized in the manner similar to Example 2.

MS (m/z): 281 (M$^+$), 280 (base).

Example 8

4-Oxo-2-(2-thienylmethyl)-3,4-dihydroquinazoline-7-carboxylic acid

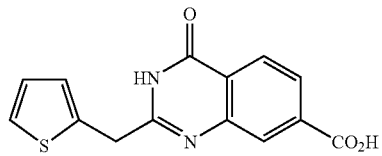

Using methyl 4-oxo-2-(2-thienylmethyl)-3,4-dihydroquinazoline-7-carboxylate which was synthesized in Production Example 8, the title compound was obtained in the manner similar to Example 2.

$^1$H-NMR (DMSO-$d_6$, δ): 4.15 (2H, s) 6.9-7.0 (1H, m), 7.0-7.1 (1H, m), 7.3-7.4 (1H, m), 7.9-8.0 (1H, m), 8.08 (1H, d, J=1.1 Hz), 8.18 (1H, d, J=8.3 Hz), 12.57 (1H, br s), 13.38 (1H, br s).

MS (m/z): 286 (M$^+$, base).

Referential Example 1

2-(3-Chlorobenzyl)-3-methyl-4-oxo-3,4-dihydro-quinazoline-7-carboxylic acid

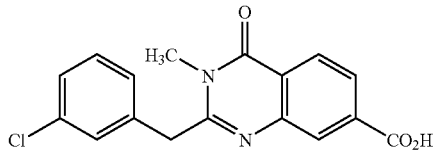

Using methyl 2-(3-chlorobenzyl)-3-methyl-4-oxo-3,4-dihydro-quinazoline-7-carboxylate which was synthesized in Production Example 9, the title compound was obtained in the manner similar to Example 1.

$^1$H-NMR (DMSO-$d_6$, δ): 3.51 (3H, s), 4.34 (2H, s), 7.2-7.5 (4H, m), 7.98 (1H, dd, J=1.4, 8.5 Hz), 8.05 (1H, d, J=1.4 Hz), 8.22 (1H, d, J=8.5 Hz), 13.43 (1H, br s).

MS (m/z): 327 (M$^+$−1, base).

Formulation Example 1

Tablet

|  | mg/tablet |
| --- | --- |
| Active ingredient | 5.0 |
| Starch | 10.0 |
| Lactose | 73.0 |
| Carboxymethyl cellulose calcium | 10.0 |
| Talc | 1.0 |
| Magnesium stearate | 1.0 |
|  | 100.0 |

The active ingredient is pulverized to a grain size not greater than 70 μm, and to which starch, lactose and carboxymethyl cellulose calcium are added and thoroughly mixed. Ten (10) % starch paste is added to the mixture, mixed by stirring and granulated. After drying, the granules are dressed to around 1000 μm in particle size. Mixing talc and magnesium stearate therewith, the blend is tableted.

The invention claimed is:

1. A quinazoline represented by the following formula:

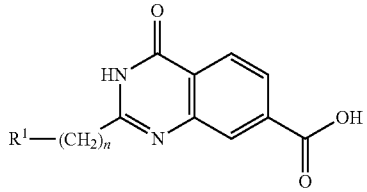

where in the formula, $R^1$ stands for phenyl or aromatic heterocyclic group which are optionally substituted with 1-3 substituents selected from halogen, $C_{1-6}$ alkyl, $C_{1-6}$ haloalkyl containing 1-6 halogen atoms and $C_{1-6}$ alkoxy; and n is an integer of 1-3;

or a salt thereof.

2. The quinazoline or salt thereof according to claim 1, in which $R^1$ stands for phenyl which is optionally substituted with 1-3 substituents selected from halogen, $C_{1-6}$ alkyl, $C_{1-6}$ haloalkyl containing 1-6 halogen atoms and $C_{1-6}$ alkoxy.

3. The quinazoline or salt thereof according to claim 1, in which n is 1.

4. A pharmaceutical composition comprising the quinazoline or salt thereof as described in claim 1, and a pharmaceutically acceptable carrier.

5. The quinazoline or salt thereof according to claim 2, in which n is 1.

6. A pharmaceutical composition comprising the quinazoline or salt thereof as described in claim 2, and a pharmaceutically acceptable carrier.

7. A pharmaceutical composition comprising the quinazoline or salt thereof as described in claim 3, and a pharmaceutically acceptable carrier.

* * * * *